US006893825B2

(12) United States Patent
Sakakibara et al.

(10) Patent No.: US 6,893,825 B2
(45) Date of Patent: May 17, 2005

(54) MICROORGANISMS FOR USE IN THE MEASUREMENT OF ENVIRONMENTAL FACTORS

(75) Inventors: Hitoshi Sakakibara, Wako (JP); Kentaro Takei, Wako (JP)

(73) Assignee: Riken, Wako (JP)

( * ) Notice: Subject to any disclaimer, the term of this patent is extended or adjusted under 35 U.S.C. 154(b) by 371 days.

(21) Appl. No.: 10/126,120

(22) Filed: Apr. 19, 2002

(65) Prior Publication Data

US 2003/0108526 A1 Jun. 12, 2003

(30) Foreign Application Priority Data

Sep. 25, 2001 (JP) ......................................... 2001-291059

(51) Int. Cl.⁷ .............................. C12Q 1/68; C12Q 1/02; C12Q 1/00; G01N 33/53
(52) U.S. Cl. .............................. 435/6; 435/29; 435/4; 435/7.91
(58) Field of Search ........................... 435/6, 29, 4, 7.91; 800/295

(56) References Cited

U.S. PATENT DOCUMENTS 6,294,714 B1 * 9/2001 Matsunaga et al. ......... 800/290

2003/0108526 A1 * 6/2003 Sakakibara et al. ........... 435/29

OTHER PUBLICATIONS

Inoue et al, LaNature[Nature], vol. 409(6823), p1060–1063, Feb. 22, 2001, (Abstract Only).*

Kentaro Takei et al., "Identification of Genes Encoding Adenylate Isopentenyltransferase, a Cytokinin Biosynthesis Enzyme, in *Arabidopsis thaliana*" *The Journal of Biological Chemistry*, vol. 276, No. 28, pp. 26405–26410 (2001).

Tomomi Suzuki et al., "The Arabidopsis Sensor His–kinase, AHK4, Can Respond to Cytokinins", *Plant Cell Physiol*, 42(2); pp. 107–113 (2001).

Hisami Yamada et al., "The Arabidopsis AHK4 Histidine Kinase is a Cytokinin–Binding Receptor that Transduces Cytokinin Signals Across the Membrane", *Plant Cell Physiol*, 42(9); pp. 1017–1023 (2001).

* cited by examiner

*Primary Examiner*—Louise N. Leary
(74) *Attorney, Agent, or Firm*—Darby & Darby

(57) ABSTRACT

A microorganism mixture consisting of a first microorganism that secretes a substance upon perception of an environmental factor and a second microorganism that expresses a marker gene upon perception of the secreted substance is disclosed. The present invention provides a means for measuring environmental factors, such as osmotic pressure, simply and with high accuracy.

19 Claims, 3 Drawing Sheets

Mixed colony of
E. coli [pTrcIPT7] and
E. coli [pIN-III-ZmHK1]

Mixed colony of
E. coli [pTrcIPT8] and
E. coli [pIN-III-ZmHK1]

MICROORGANISMS FOR USE IN THE MEASUREMENT OF ENVIRONMENTAL FACTORS

BACKGROUND OF THE INVENTION

1. Technical Field

The present invention relates to microorganism mixtures and microorganisms for use in the measurement of environmental factors. Simple and highly accurate measurement of environmental factors becomes possible by using the microorganism mixtures or microorganisms of the invention.

2. Prior Art

Any organism, irrespective of being a microorganism, animal or plant, is equipped with mechanisms for sensing minute changes or specific chemical substances in the external environment. Specifically, sensors specific to individual factors present on the surfaces of cell membranes or inside of cells percept the presence (or changes) of those factors, transfer that information to the promoters of relevant genes through transcription regulatory factors, and switch on or off the expression of the target genes. Thus, organisms cope with environmental changes. Recent advances in molecular biology have elucidated a large number of sensor proteins of procaryotes and eucaryotes involved in perception of external environment, as well as transcription regulatory factors functioning downstream of these proteins and promoter sequences of the target genes of such factors. These sensor proteins include proteins that detect changes in physico-chemical states such as oxygen level or osmotic pressure; proteins that percepts the presence or absence of specific substances such as phosphate ions, nitrate ions or heavy metal ions; and proteins that sense such substances as hormones occurring in nature only in extremely small quantities. On the other hand, identification of genes involved in the synthesis of hormones exhibiting physiological activity in extremely small quantities has also progressed.

It is believed that plants have evolved diversified perception systems for external environment because they are organisms unable to immigrate. Actually, it is presumed that plants have several hundred environmental sensor genes according to information about the genome of *Arabidopsis thaliana*. It is expected that the entire picture of the potential sensing functions plants have will be elucidated at the molecular level in near future.

SUMMARY OF THE INVENTION

The present invention has been achieved by combining those bioresources as described above that organisms potentially have and are involved in the perception of the external environment. It is an object of the present invention to provide a means for measuring various factors in the environment simply and with highly accuracy.

As a result of extensive and intensive researches toward the solution of the above problem, the present inventors have found that it is possible to create a biosensor capable of measuring environmental factors with high accuracy by combining the following microorganisms:
(i) a microorganism harboring a plasmid comprising a cytokinin synthesis gene under the control of a promoter that is controlled in an external environmental factor-dependent manner; and
(ii) a microorganism equipped with a cytokinin detection system.

Thus, the present invention has been achieved.

The present invention relates to a microorganism mixture consisting of a first microorganism that secretes a substance upon perception of an environmental factor and a second microorganism that expresses a marker gene upon perception of the substance secreted.

The present invention also relates to a microorganism that secretes a substance upon perception of an environmental factor and expresses a marker gene upon perception of the substance secreted.

Further, the present invention relates to a method of measuring an environmental factor, comprising mixing the above-described microorganism mixture or microorganism with a sample and measuring the environmental factor in the sample from the expression level of the marker gene.

DESCRIPTION OF THE PREFERRED EMBODIMENT

Figure 1:
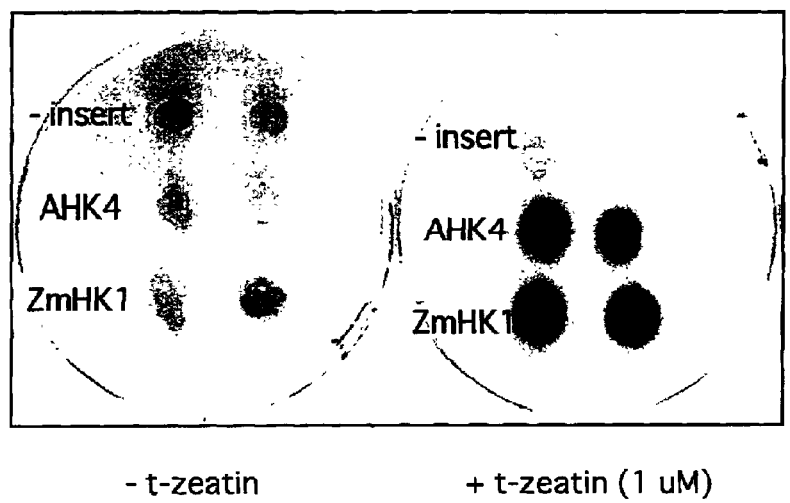
FIG. 1 is a photograph showing the experimental results of Example 4.

Hereinbelow, the present invention will be described in detail.

The microorganism mixture of the invention consists of a first microorganism that secretes a substance upon perception of an environmental factor (hereinafter, referred to as "sensor microorganism") and a second microorganism that expresses a marker gene upon perception of the substance secreted (hereinafter, referred to as "marker microorganism").

The term "environmental factor" refers to a substance present in the environment or a state of the environment. For example, substances such as oxygen, phosphate ions, nitrate ions, nickel ions, copper ions, amino acids, etc. and states such as osmotic pressure, temperature, pH, etc. are encompassed in this term.

A substance to be secreted (hereinafter, sometimes referred to as a "secretion substance") may be any substance as long as information about its secretion can be transmitted from a sensor microorganism to a marker microorganism. Preferably, the secretion substance is a plant hormone. Since a marker microorganism can perceive a plant hormone even if the amount of secretion from a sensor microorganism is extremely small, it is suitable for measuring substances of extremely small quantities or minute changes in states. Specific examples of plant hormones include cytokinins, ethylene, auxins and abscisic acid.

As a marker gene, any gene may be used as long as the presence or absence, the amount, etc. of an environmental factor of interest can be finally confirmed or measured with it. For example, a pigment gene, luminescence gene, fluorescence gene or the like may be used. More specifically, β-galactosidase gene, luciferase gene, green fluorescence protein (GFP) gene or the like may be used.

As a microorganism, a bacterium or yeast may be used. Alternatively, a cultured cell of a higher animal or plant may be used. Since the microorganism of the invention is subjected to various genetic engineering in many cases, it is most preferable to use *Escherichia coli* in which genetic engineering is easy.

As a sensor microorganism, a microorganism having a gene of an enzyme that synthesizes a substance to be secreted and a mechanism that allows the gene to be expressed in response to an environmental factor may be used, for example.

As a gene of an enzyme that synthesizes a substance to be secreted (hereinafter, referred to as a "secretion substance synthesis enzyme gene"), a plant hormone synthesis enzyme gene is preferable. Specific examples of plant hormone synthesis enzyme genes include the genes of the following enzymes:

Cytokinins: *Arabidopsis thaliana*-derived adenylate isopentenyltransferases (AtIPT1, AtIPT3, AtIPT4, AtIPT5, AtIPT6, AtIPT7 and AtIPT8), *Agrobacterium*-derived adenylate isopentenyltransferase (Tmr)

Ethylene: tomato-derived 1-aminocyclopropane-1-carboxylate synthases (LeACS1A, LeACS1B, LeACS2, LeACS3, LeACS4, LeACS5 and LeACS6), tomato-derived 1-aminocyclopropane-1-carboxylate oxidases (LeACO1, LeACO2 and LeACO3)

Auxins: *Arabidopsis thaliana*-derived aromatic amino acid decarboxylase (AADC), *Arabidopsis thaliana*-derived amine oxidase (CAO), maize-derived aldehyde oxidase (AO)

Abscisic acid: tomato-derived zeaxanthin epoxidase (ABA2), maize-derived 9-cis-epoxycarotenoid dioxygenase (VP14).

The above-described enzymes and genes thereof have already been known as shown in the Table below. One of ordinary skill in the art can use these enzymes and genes appropriately, if necessary.

TABLE 1

| Enzyme | Accession No. | Reference |
|---|---|---|
| AtIPT1 | BAB59040 | The Journal of Biological Chemistry Vol.276,No.28, pp26405–26410,2001 |
| AtIPT3 | BAB59043 | |
| AtIPT4 | BAB59044 | |
| AtIPT5 | BAB59041 | |
| AtIPT6 | BAB59045 | |
| AtIPT7 | BAB59046 | |
| AtIPT8 | BAB59047 | |
| Tmr | AB016260 | Biochem. Biophys. Acta 1998 vol. 1396:1–7 |
| LeACS1A | U72389 | Proceeding of National Academy of Science, U.S.A. Vol. 89, No.6, pp2475–2479, 1992 |
| LeACS1B | U72390 | |
| LeACS2 | M83318 | |
| LeACS3 | M83320 | Proceeding of National Academy of Science, U.S.A. Vol. 88, No.12, pp5340–5344, 1991 |
| LeACS4 | M63490 | |
| LeACS5 | M83322 | |
| LeACS6 | U74461 | Plant Molecular Biology Vol. 34, No.2, pp275–286, 1997 |
| LeACO1 | X58273 | European Journal of Biochemistry Vol. 253, No.1, pp20–26, 1998 |
| LeACO2 | Y00478 | |
| LeACO3 | X04792 | |
| AADC | CAB81456 | |
| CAO | NP_192966 | No reference |
| AO | E15856 | |
| ABA2 | Q40412 | EMBO Journal Vol. 15, No.10, pp2331–2342, 1996 |
| VP14 | AAB62181 | Proceeding of National Academy of Science, U.S.A. Vol. 94, No.22, pp12235–12240, 1997 |

At the time of filing of the present patent application, a large number of mechanisms were known which allow a secretion substance synthesis enzyme gene to be expressed in response to an environmental factor. In the present invention, these mechanisms may be used. Specifically, the following mechanisms may be enumerated.

(i) Mechanism that Allows a Secretion Substance Synthesis Enzyme Gene to be Expressed in Response to Osmotic Pressure

*E. coli* has a mechanism that controls the expression of a specific gene (ompC gene) in response to the strength of osmotic pressure in the external environment by means of EnvZ (an osmotic pressure sensor protein) and OmpR (a transcription regulatory factor). By utilizing this EnvZ-OmpR system, it is possible to create a mechanism that allows a secretion substance synthesis enzyme gene to be expressed in response to osmotic pressure. Briefly, a microorganism having genes encoding EnvZ and OmpR and the promoter of ompC gene is created. Then, a secretion substance synthesis enzyme gene is integrated downstream of the promoter of ompC gene. Thus, an osmotic pressure-responsive mechanism can be constructed.

By using this mechanism, the strength of osmotic pressure in the environment can be judged from the expression level of a marker gene. It is also possible to estimate the value of osmotic pressure in the environment by comparing the expression level of the marker gene in a test sample with that in a control sample of which the osmotic pressure is known.

(ii) Mechanism that Allows a Secretion Substance Synthesis Enzyme Gene to be Expressed in Response to Oxygen

*E. coli* has a mechanism that allows a specific gene (sdh gene) to be expressed when oxygen concentration in the external environment has exceeded a specific level by means of ArcB (an oxygen sensor protein) and ArcA (a transcription regulatory factor). Therefore, it is possible to construct an oxygen-responsive mechanism by creating a microorganism having genes encoding ArcB and ArcA and the promoter of sdh gene, and integrating a secretion substance synthesis enzyme gene downstream of the promoter of sdh gene.

By using this mechanism, it is possible to judge whether oxygen concentration in the environment is beyond a specific level or not based on the expression level of a marker gene. It is also possible to estimate the value of oxygen concentration in the environment by comparing the expression level of the marker gene in a test sample with that in a control sample of which oxygen concentration is known.

(iii) Mechanism that Allows a Secretion Substance Synthesis Enzyme Gene to be Expressed in Response to Phosphate Ions

*E. coli* has a mechanism that allows a specific gene (PhoA gene) to be expressed when phosphate ion concentration in the external environment is below a specific level by means of PhoR (a phosphate ion sensor protein) and PhoB (a transcription regulatory factor). Therefore, it is possible to construct a phosphate ion-responsive mechanism by creating a microorganism having genes encoding PhoR and PhoB and the promoter of PhoA gene, and integrating a secretion substance synthesis enzyme gene downstream of the promoter of PhoA gene.

By using this mechanism, it is possible to judge whether phosphate ion concentration in the environment is below a specific level or not based on the expression level of a marker gene. It is also possible to estimate the value of phosphate ion concentration in the environment by comparing the expression level of the marker gene in a test sample with that in a control sample of which phosphate ion concentration is known.

(iv) Mechanism that Allows a Secretion Substance Synthesis Enzyme Gene to be Expressed in Response to Nitrate Ions

*E. coli* has a mechanism that allows a specific gene (narK gene) to be expressed when nitrate ion concentration in the external environment has exceeded a specific level by means of NarX (a nitrate ion sensor protein) and NarL (a transcription regulatory factor). Therefore, it is possible to construct a nitrate ion-responsive mechanism by creating a microorganism having genes encoding NarX and NarL and the promoter of narK gene, and integrating a secretion substance synthesis enzyme gene downstream of the promoter of narK gene.

By using this mechanism, it is possible to judge whether nitrate ion concentration in the environment is beyond a specific level or not based on the expression level of a marker gene. It is also possible to estimate the value of nitrate ion concentration in the environment by comparing the expression level of the marker gene in a test sample with that in a control sample of which nitrate ion concentration is known.

(v) Mechanism that Allows a Secretion Substance Synthesis Enzyme Gene to be Expressed in Response to Nickel Ions E. coli has a mechanism that allows nickel ions to be taken in by means of NikABCDE (a nickel ion transporter protein) and suppresses the expression of a specific gene (nikABCDE gene) when nickel ion concentration in the external environment has exceeded a specific level by means of a nickel ion-dependant transcription activator (NikR). Therefore, it is possible to construct a nickel ion-responsive mechanism by creating a microorganism having genes encoding NikABCD and NikR and the promoter of nikAB-CDE gene, and integrating a secretion substance synthesis enzyme gene downstream of the promoter of nikABCDE gene.

By using this mechanism, it is possible to judge whether nickel ion concentration in the environment is beyond a specific level or not based on the expression level of a marker gene. It is also possible to estimate the value of nickel ion concentration in the environment by comparing the expression level of the marker gene in a test sample with that in a control sample of which nickel ion concentration is known.

(vi) Mechanism that Allows a Secretion Substance Synthesis Enzyme Gene to be Expressed in Response to Copper Ions E. coli has a mechanism that allows a specific gene (cusCFBA gene) to be expressed when copper ion concentration in the external environment has exceeded a specific level by means of CusS (a copper ion sensor protein) and CusR (a transcription regulatory factor). Therefore, it is possible to construct a copper ion-responsive mechanism by creating a microorganism having genes encoding CusS and CusR and the promoter of cusCFBA gene, and integrating a secretion substance synthesis enzyme gene downstream of the promoter of cusCFBA gene.

By using this mechanism, it is possible to judge whether copper ion concentration in the environment is beyond a specific level or not based on the expression level of a marker gene. It is also possible to estimate the value of copper ion concentration in the environment by comparing the expression level of the marker gene in a test sample with that in a control sample of which copper ion concentration is known.

The above-described enzymes, genes and promoters have already been known as shown in the Table below. One of ordinary skill in the art can use these enzymes, etc. appropriately, if necessary.

TABLE 2

| Designation | Accession No. | Reference |
| --- | --- | --- |
| EnvZ | AAA16242 | Journal of Bacteriology Vol. 174, No.5, pp1522–1527, 1992 |
| OmpR | AAA16241 | |

TABLE 2-continued

| Designation | Accession No. | Reference |
| --- | --- | --- |
| OmpC | P06996 | Journal of Biological Chemistry Vol. 258 No.11, pp6932–6940, 1983 |
| OmpF | P02931 | Nucleic Acid Research Vol. 10, No.21, pp6957–6968, 1982 |
| ArcB | P22763 | Molecular Microbiology Vol. 4, No.5, pp715–727, 1990 |
| ArcA | P03026 | Journal of Biological Chemistry Vol. 260, No.7, pp4236–4242, 1985 |
| Sdh | P10446 | Biochemical Journal Vol. 222, No.2, pp519–534, 1984 |
| PhoR | P08400 | Journal of Molecular Biology Vol. 192, No.3, pp549–556, 1986 |
| PhoB | P08402 | Journal of Molecular Biology Vol. 190, No.1, pp37–44, 1986 |
| PhoA | AAC73486 | Science Vol.277, No.5331, pp1453–1474, 1997 |
| narX | P10956 | Nucleic Acid Research Vol. 17, No.8, pp2947–2957, 1989 |
| narL | P10957 | |
| nark | P10903 | FEBS Letter Vol. 252, No.1–2, pp139–143, 1989 |
| NikA | P33590 | Molecular Microbiology Vol. 9, No.6, 1181–1191, 1993 |
| NikB | P33591 | |
| NikC | P33592 | |
| NikD | P33593 | |
| NikE | P33594 | |
| NikR | CAA70150 | Journal of Bacteriology Vol. 181, No.2, 670–674, 1999 |
| CusS | P77485 | Journal of Bacteriology Vol. 182, No.20, 5864–5871, 2000 |
| CusR | P77380 | |
| CusCFBA | P77211 | Science Vol.277, No.5331, pp1453–1474, 1997 |

As a marker microorganism, a microorganism having a mechanism that allows a marker gene to be expressed in response to a secreted substance may be used, for example. The mechanism that allows a marker gene to be expressed in response to a secreted substance may be created by modifying a binary control system that the microorganism has and the target gene of the system. Briefly, the sensor protein of the binary control system is replaced with a protein that phosphorylates a secreted substance upon perception of its secretion; and the gene controlled by the binary control system is replaced with a marker gene. Thus, a mechanism that allows the marker gene to be expressed in response to the secreted substance can be constructed.

Specific examples of binary control systems useful in the invention include the following systems.

TABLE 3

| Binary Control System | Original Source | Target Gene |
| --- | --- | --- |
| rcsC-yojN-rcsB | E. coli | Cps (wza) gene |
| SLN1-YPD1-SSK1 | Budding yeast | GPD1 gene |

Specific examples of sensor proteins to be replaced with the sensor protein of a binary control system include the following proteins.

TABLE 4

| Sensor Protein | Original Source | Substance to be Perceived |
| --- | --- | --- |
| AHK4 | Arabidopsis thaliana | Cytokinin |
| ZmHK1 | Maize | Cytokinin |
| ETR1 | Arabidopsis thaliana | Ethylene |
| ERS1 | Arabidopsis thaliana | Ethylene |

Of the above sensor proteins, ZmHK1 may be preferable. Since this protein is able to perceive extremely small amounts of cytokinins (its ability is approximately 10-fold compared to that of AHK4), this protein is suitable for the measurement of extremely small amounts of environmental factors.

The above-described enzymes, genes, etc. have already been known as shown in the Table below. One of ordinary skill in the art can use these enzymes, etc. appropriately, if necessarily.

TABLE 5

| Designation | Accession No. | Reference |
| --- | --- | --- |
| RcsC | P14376 | Journal of Bacteriology, Vol. 172, No.2, pp659–669, 1990 |
| YojN | P39838 | Science Vol.277, No.5331, pp1453–1474, 1997 |
| RcsB | P14374 | Journal of Bacteriology, Vol. 172, No.2, pp659–669, 1990 |
| Cps(wza) | P76388 | Science Vol.277, No.5331, pp1453–1474, 1997 |
| Sln1 | S48387 | Science, Vol. 262, No.5133, pp566–569, 1993 |
| Ypd1 | AAC49440 | Cell, Vol. 86, No.6, pp865–875, 1996 |
| Ssk1 | Q07084 | Nature, Vol. 369, No. 6477, pp242–245, 1994 |
| Gpd1 | Q00055 | Molecular Microbiology, Vol. 10, No.5, pp1101–1111, 1993 |
| AHK4 | BAB40776 | Plant Cell physiology, Vol. 42, No.2, pp107–113, 2001 |
| ZmHK1 | BAB20583 | No reference |
| ETR1 | P49333 | Science, Vol. 262, No.5133, pp539–594, 1993 |
| ERS1 | AAK96723 | Science, Vol. 269, pp1712–1714, 1995 |

As described above, the microorganism mixture of the invention consists of two types of microorganisms, i.e. a sensor microorganism and a marker microorganism. In another aspect of the invention, a single microorganism may have the functions of these two microorganisms.

The microorganism mixture or microorganism of the invention may be used in the measurement of environmental factors. When the microorganism mixture or microorganism of the invention is mixed with a sample having an environmental factor to be measured, the expression level of a marker gene varies responding to the environmental factor. Therefore, it is possible to measure the environmental factor using changes in the expression level as an indicator.

EXAMPLE 1

Cytokinin Synthesis by *E. coil*

1-1 Construction of Cytokinin Synthesis Gene Expression Systems

Using adenylate isopentenyltransferase cDNAs (AtIPT1 and AtIPT3 through AtIPT8) isolated from *Arabidopsis thaliana* ecotype Columbia and Agrobacterium IPT gene tmr (pTi-SAKURA; Biochim, Biophys, Acta 1998, Vol. 1396: 1–7) as templates, the protein coding regions of the individual genes were amplified by PCR. Primer sequences used in the reactions are as described below.

AtIPT1:
(SEQ ID NO:3)
5'-TCATGACAGAACTCAACTTCCACC-3'

(SEQ ID NO:4)
5'-ATAAAGCTTCTAATTTTGCACCAAATGCCGC-3'

AtIPT3:

(SEQ ID NO:5)
5'-CGCGGATCCATCATGATTATGAAGATATCTATGGC-3'

(SEQ ID NO:6)
5'-GCGCTCGAGCTGATCACGCCACTAGACACCG-3'

AtIPT4:
(SEQ ID NO:7)
5'-TCATGAAGTGTAATGACAAAATGG-3'

(SEQ ID NO:8)
5'-ATAGTCGACGTTTTGCGGTGATATTAGTCC-3'

AtIPT5:
(SEQ ID NO:9)
5'-GGGATCATGAAGCCATGCATGACGGC-3'

(SEQ ID NO:10)
5'-GCGCTCGAGTTACCTCACCGGGAAATCGC-3'

AtIPT6:
(SEQ ID NO:11)
5'-CAACAACTCATGACCTTGTTATCACC-3'

(SEQ ID NO:12)
5'-GGCCAAGCTTGGAAAAACAGACTAAACTTCC-3'

AtIPT7:
(SEQ ID NO:13)
5'-GGCGGATCCTCATGAAGTTCTCAATCTCATC-3'

(SEQ ID NO:14)
5'-GGCCTGCAGCTTTTCATATCATATTGTGGGC-3'

AtIPT8:
(SEQ ID NO:15)
5'-CAAAATCTTACGTCCACATTCGTCTC-3'

(SEQ ID NO:16)
5'-CCGGCTGCAGCTCACACTTTGTCTTTCACC-3' tmr:
(SEQ ID NO:17)
5'-CGCAAAAAACCCATGGATCTGCGTC-3'

(SEQ ID NO:18)
5'-CGAACATCGGATCCAAATGAAGACAGG-3'

After digestion of each of the amplified DNA fragments at the restriction enzyme sites created on primers, the fragment was ligated to a vector plasmid pTrc99A (Amersham Pharmacia Biotech) designed for expressing a foreign protein in *E. coli*. When introduced into *E. coli*, this vector comes under the control of a regulatory mechanism *E. coli* innately has that activates the expression of lac operon genes. There, this vector can perceive IPTG (isopropyl-β-D-thiogalactopyranoside) in the medium and express the foreign gene inserted. The thus constructed plasmids were designated pTrcIPT1, pTrcIPT3 through pTrcIPT8, and pTrctmr, respectively. In a similar manner, another set of expression plasmids were constructed using an *E. coli* expression vector pQE30 (Qiagen) and designated pQEIPT1, pQEIPT3 through pQEIPT8, respectively. The protein coding regions of the individual genes were amplified by PCR. The primer sequences used in the reactions are as described below.

atIPT1:
(SEQ ID NO:19)
5'- ATAGGATCCCTAATGACAGAACTCAACTTCC-3'

(SEQ ID NO:20)
5'- ATAAAGCTTCTAATTTTGCACCAAATGCCGC-3'

-continued

AtIPT3:
                    (SEQ ID NO:21)
5'- GCGGGATCCATGATCATGAAGATATCTATGG-3'

(SEQ ID NO:22)
5'- GCGCTCGAGCTGATCACGCCACTAGACACCG-3'

AtIPT4:
                    (SEQ ID NO:23)
5'- ATAGGTACCATTTACGACATGAAGTGTAATGAC-3'

(SEQ ID NO:24)
5'- ATAGTCGACGTTTTGCGGTGATATTAGTCC-3'

AtIPT5:
                    (SEQ ID NO:25)
5'- GCGGGATCCATGAAGCCATGCATGACGGC-3'

(SEQ ID NO:26)
5'- GCGCTCGAGTTACCTCACCGGGAAATCGC-3'

AtIPT6:
                    (SEQ ID NO:27)
5'- GCGAGATCTATGCAACAACTCATGACC-3'

(SEQ ID NO:28)
5'- GCGCTCGAGGGAAAAACAGACTAAACTTCC-3'

AtIPT7:
                    (SEQ ID NO:29)
5'- GCGGGATCCATGAAGTTCTCAATCTCATCAC-3'

(SEQ ID NO:30)
5'- GCGCTCGAGCTTTTCATATCATATTGTGGGC-3'

AtIPT8:
                    (SEQ ID NO:31)
5'- GCGGGATCCATGCAAAATCTTACGTCCAC-3'

(SEQ ID NO:32)
5'-CCGGCTGCAGCTCACACTTTGTCT
        GCGCTCGAGCTCACACTTTGTCTTTCACC-3'

Plasmid pQE30 also has an IPTG-inducible promoter. Each of the resultant plasmids was transformed into *E. coli* JM109.

1-2 Cytokinin Synthesis by *E. coli* Transformants

The *E. coli* transformants prepared with the individual IPT genes were cultured in modified M9 minimum medium (M9 salts, 1 M sorbitol, 1% casamino acids, 2% sucrose, 2.5 mM betaine, 5 μg/ml thiamin, 1 mM $MgSO_4$, 0.1 mM $CaCl_2$, 20 μg/ml ampicillin) overnight at 25° C. Subsequently, 0.5 ml of this overnight culture was added to 10 ml of fresh modified M9 minimum medium and cultured until ABSORBANCE AT 600 NM reached 0.5. IPTG was added thereto to give a concentration of 1 mM, and cells were cultured for another 4 hr at 25° C. As a control, cells were cultured without the addition of IPTG. The resultant culture broth was centrifuged at 3000×g for 10 min to recover the supernatant.

The cytokinin molecule species in the recovered supernatant were quantitatively determined according to the method of Takei et al. (Plant Cell Physiology 2001, Vol. 42: 85–93). The results are shown in Tables 6 and 7 below.

TABLE 6

Cytokinin Contents in *E. coli* Culture Supernatant
(A) pTrc99A-Based Vectors

| | | Amount of cytokinin detected in medium | |
|---|---|---|---|
| | | t-zeatin | iP |
| Expression vector | IPTG | (pmol / mL culture) | |
| pTrctmr | + | 11.0 | 48.0 |
| | − | N.T. | N.T. |
| pTrcTPT1 | + | 76.1 | 313.9 |
| | − | N.T. | N.T. |
| pTrcIPT3 | + | 9.9 | 106.7 |
| | − | N.T. | N.T. |
| pTrcIPT4 | + | 199.2 | 220.6 |
| | − | N.T. | N.T. |
| pTrcIPT5 | + | 0 | 328.0 |
| | − | N.T. | N.T. |
| pTrcIPT6 | + | 0 | 4.1 |
| | − | N.T | N.T |
| pTrcIPT7 | + | 45.7 | 673.6 |
| | − | N.T. | N.T. |
| pTrcIPT8 | + | 65.0 | 369.7 |
| | − | N.T. | N.T. |

N.T.: not tested.
iP: isopentenyladenosine
Note: Both t-zeatin and iP are cytokinin molecule species having physiological activity.

TABLE 7

Cytokinin Contents in *E. coli* Culture Supernatant
(B) pQE30-Based Vectors

| | | Amount of cytokinin detected in medium | |
|---|---|---|---|
| | | t-zeatin | iP |
| Expression vector | IPTG | (pmol / mL culture) | |
| pQE30 | + | 0 | 4.9 |
| pQEIPT1 | + | 59.6 | 674.1 |
| | − | 6.6 | 609.8 |
| pQEIPT3 | + | 10.4 | 87.7 |
| | − | 6.0 | 34.3 |
| pQEIPT4 | + | 906.4 | 174.8 |
| | − | N.T. | N.T |
| pQEIPT5 | + | 13.3 | 684.5 |
| | − | 6.6 | 589.0 |
| pQEIPT6 | + | N.T. | N.T |
| | − | N.T | N.T |
| pQEIPT7 | + | 67.3 | 826.1 |
| | − | 5.0 | 61.9 |
| pQEIPT8 | + | 7.4 | 496.9 |
| | − | 0 | 14.4 |

N.T.: not tested

Cytokinins were released into the medium even in the absence of IPTG. This resulted from insufficient repression by *E. coli* lacI repressor attributable to a large number of copies of the introduced plasmid in *E. coli*. It is believed that this can be easily improved by using a plasmid with a less number of copies or by using other signal recognition/control system.

Even when pQE plasmids were used, the transformants prepared with pQEIPT7 and pQEIPT8, respectively, exhibited remarkable differences in the amounts of cytokinins released in the presence and absence of IPTG.

EXAMPLE 2

Cytokinin Synthesis by Budding Yeast
2-1. Construction of Cytokinin Synthesis Gene Expression Systems Using the above-described adenylate isopentenyltransferase cDNAs (AtIPT1 and AtIPT3 through AtIPT8) as templates, the protein coding regions of the individual genes were amplified by PCR. Primer sequences used in the reactions are as described below.

```
AtIPT1:
                                        (SEQ ID NO:33)
5'-GCGGGATCCATGACAGAACTCAACTTCCACC-3'

(SEQ ID NO:34)
5'-GCGCTCGAGCTAATTTTGCACCAAATGCCGC-3'

ATIPT3:
                                        (SEQ ID NO:35)
5'- GCGGGATCCATGATCATGAAGATATCTATGG-3'

(SEQ ID NO:36)
5'- GCGCTCGAGCTGATCACGCCACTAGACACCG-3'

ATIPT4:
                                        (SEQ ID NO:37)
5'- GCGAGATCTATGAAGTGTAATGACAAAATGG-3'

(SEQ ID NO:38)
5'- GCGCTCGAGTGTTTTGCGGTGATATTAGTCC-3'

ATIPT5:
                                        (SEQ ID NO:39)
5'- GCGGGATCCATGAAGCCATGCATGACGGC-3'

(SEQ ID NO:40)
5'- GCGCTCGAGTTACCTCACCGGGAAACTCGC-3'

ATIPT6:
                                        (SEQ ID NO:41)
5'-GCGAGATCTATGCAACAACTCATGACC-3'

(SEQ ID NO:42)
5'-GCGCTCGAGGGAAAAACAGACTAAACTTCC-3'

ATIPT7:
                                        (SEQ ID NO:43)
5'- GCGGGATCCATGAAGTTCTCAATCTCATCAC-3'

(SEQ ID NO:44)
5'- GCGCTCGAGCTTTTCATATCATATTGTGGGC-3'

ATIPT8:
                                        (SEQ ID NO:45)
5'- GCGGGATCCATGCAAAATCTTACGTCCAC-3'

(SEQ ID NO:46)
5'- GCGCTCGAGCTCACACTTTGTCTTTCACC-3'
```

After digestion with BamHI and XhoI, each of the amplified DNA fragments was ligated to the BamHI/XhoI site of a vector plasmid pYES2 (Invitrogen) designed for expressing a foreign protein in yeast. This vector has GAL1 promoter and, when introduced into yeast, comes under the control of a regulatory mechanism of yeast itself involved in the use of galactose. There, this vector can perceive galactose in the medium and express the foreign gene inserted in it. The thus constructed plasmids were designated pYESIPT1 and pYESIPT3 through pYESIPT8, respectively.

Each of the resultant plasmids was transformed into yeast MT8 strain.

2-2. Cytokinin Synthesis by Yeast Transformants

The yeast transformants prepared with the individual IPT genes were cultured in SC-ura+glu minimum medium (0.67% yeast nitrogen base, 2% glucose, 0.01% each of adenine, arginine, cysteine, leucine, lysine, threonine and tryptophan, 0.005% each of aspartic acid, histidine, isoleucine, methionine, phenylalanine, proline, serine, tyrosine and valine) overnight at 28° C. Subsequently, 0.5 ml of this overnight culture was added to 10 ml of SC-ura+glu minimum medium and cultured until ABSORBANCE AT 600 NM reached 0.5. After centrifugation of the culture broth, the supernatant was discarded. The cell pellet was suspended in 10 ml of SC-ura+gal minimum medium (2% glucose in SC-ura+glu medium is replaced with 2% galactose+2% raffinose) and cultured for another 4 hr at 28° C. As a control, cells were cultured in SC-ura+glu minimum medium without the shift to SC-ura+gal minimum medium. The resultant culture broth was centrifuged at 3000×g for 10 min to recover the supernatant.

The cytokinin molecule species in the recovered supernatant were quantitatively determined in the same manner as in Example 1. The results are shown in Table 8.

TABLE 8

Cytokinin Contents in Yeast Culture Supernatant

| Expression vector | Carbon source in medium | Amount of cytokinin detected in medium | |
|---|---|---|---|
| | | iPA | iP |
| | | (pmol / mL culture) | |
| pYES2 (control) | gal + raf | 0 | 0 |
| pYESIPT1 | glu | N.T. | N.T. |
| | gal + raf | 14.7 | 115.2 |
| pYESIPT3 | glu | N.T. | N.T. |
| | gal + raf | 1.5 | 22.7 |
| pYESIPT4 | glu | N.T. | N.T. |
| | gal + raf | 157.2 | 688.6 |
| pYESIPT5 | glu | N.T. | N.T. |
| | gal + raf | 0 | 9.1 |
| pYESIPT6 | glu | N.T. | N.T. |
| | gal + raf | N.T. | N.T. |
| pYESIPT7 | glu | N.T. | N.T. |
| | gal + raf | 2.6 | 24.9 |
| pYESIPT8 | glu | N.T. | N.T. |
| | gal + raf | 0 | 10.4 | glu: glucose, gal + raf: galactose + raffinose
iPA: isopentenyladenosine (a cytokinin molecule species having physiological activity)

When the transformants were induced in the medium containing galactose+raffinose as carbon sources, a significant amount of iP or iPA was detected in the culture supernatant of each transformant. These results revealed that cytokinin(s) (iP and/or iPA) is/are also released into the medium even when AtIPT gene is expressed in yeast. t-Zeatin detected in the *E. coli* culture supernatant was not detected. The reason why different cytokinin species are released depending on the host microorganism is currently unknown.

From the above results, it has become clear that even when AtIPT gene is expressed in a budding yeast (*Saccharomyces cerevisiae*), a eucaryotic unicellular organism, cytokinins are also released into the medium as released when the gene is expressed in *E. coli*. Therefore, when an environmental factor perception mechanism and its regulatory gene found in eucaryotes (including plants and animals) are introduced into a budding yeast, it is possible to allow the budding yeast to synthesize a cytokinin(s) under the control of the mechanism and the regulatory gene. The resource of environmental sensor is widely useful in both procaryotes and eucaryotes.

EXAMPLE 3

Isolation of Maize Cytokinin Receptor

Sequences resembling a DNA sequence encoding an *Arabidopsis thaliana* cytokinin receptor were searched for through maize ETS (expression sequence tag) databases to thereby find one sequence (GenBank Accession No. AI861678). Since this sequence is a partial sequence representing only about ¼ of the entire sequence, a cDNA library prepared from maize green leaves was screened in order to isolate a full-length clone. DNA fragments used as probes in plaque hybridization were obtained by RT-PCR. Primer sequencers used in the PCR are as described below.

5'-GAAGAACGGTCAGTTGTCGGATG-3'    (SEQ ID NO:47)

5'-GATTGATGAATGAGAAGTCCGG-3'    (SEQ ID NO:48)

Of the positive clones obtained from the screening of 1×10⁶ clones, the largest clone pZmHK1 was subjected to determination of its entire nucleotide sequence. This clone had a cDNA insert of 3041 bp in full length and was expected to encode a protein consisting of 974 amino acids. The predicted amino acid sequence of the protein showed 57.6% identity at the amino acid level with AHK4, an *Arabidopsis thaliana* cytokinin receptor. The full-length nucleotide sequence of pZmHK1 is shown in SEQ ID NO: 1, and the predicted amino acid sequence of the protein encoded thereby is shown in SEQ ID NO: 2. These sequences are also disclosed in GenBank (Accession No. AB042270).

EXAMPLE 4

Identification of the Cytokinin Sensor Function of ZmHK1

The protein coding region of pZmHK1 was amplified by PCR and ligated to the BamHI/BSalI site of pIN-IIIΔEH plasmid. Primer sequences used in the PCR amplification are as described below.

5'-CTGATCAGATGGGGGGCAAGTACC-3'    (SEQ ID NO:49)

5'-CCTCGAGTCAAACAGCCGAATCT-3'    (SEQ ID NO:50)

Plasmid pIN-IIIΔEH has a promoter that constitutively directs weak expression of a foreign gene in *E. coli*. The resultant plasmid was designated pIN-III-ZmHK.

The constructed plasmid was transformed into E. coli KMI001 [ΔrcsC, cps::lacZ]. This *E. coli* strain is a strain in which cps gene involved in polysaccharide synthesis and a binary regulatory factor consisting of rcsC-rcsB (an expression regulatory system for cps) are partially modified. Specifically, sensor histidine kinase gene rcsC is deleted, and β-galactosidase (a marker gene) is inserted downstream of the promoter of cps gene. The resultant transformant was cultured in 2 ml of LAG liquid medium (1% Bacto tryptone, 0.5% Bacto yeast extract, 1% NaCl, 40 mM glucose, 50 mM phosphate buffer, pH 7.0) overnight at 25° C. The resultant culture broth was centrifuged and the supernatant was discarded. The *E. coli* cell pellet was washed twice in sterilized water and suspended in 2 ml (final volume) of sterilized water. This suspension was spotted at two points each on LAGX agar medium (1% Bacto tryptone, 0.5% Bacto yeast extract, 1% NaCl, 40 mM glucose, 50 mM phosphate buffer, pH 7.0, 80 μg/ml X-gal, 1.5% agarose) containing 1 μM trans-zeatin (t-zeatin) and on LAGX agar medium not containing t-zeatin, and cultured overnight (12 hr) at 25° C. The next day, the color of each colony was observed. FIG. 1 shows the state of each colony.

As shown in FIG. 1, ZmHK1-transferred *E. coli* expressed β-galactosidase in response to the cytokinin in the medium. In this regard, ZmHK1 functioned in the same manner as AHK4 that had already been identified as a cytokinin receptor of *Arabidopsis thaliana*. Accordingly, it was judged that ZmHI1, a cytokinin receptor in maize, is able to function also as a cytokinin sensor in *E. coli* KMI001 strain.

EXAMPLE 5

Assay of the Sensitivity of ZmHK1 to Cytokinin

The ZmHK1-transferred *E. coli* spot shown in FIG. 1 exhibited apparently more intensive color development than AHK4-transferred *E. coli* spots. Then, the present inventors examined whether there is any difference between ZmHK1 and AHK4 in sensitivity to a cytokinin. It is reported that AHK4-transferred *E. coli* is able to respond to approx. 50 nM t-zeatin at the lowest under the experimental conditions as described in Example 4 (Plant Cell Physiol, 2001, Vol. 42: 107–113).

Figure 2:
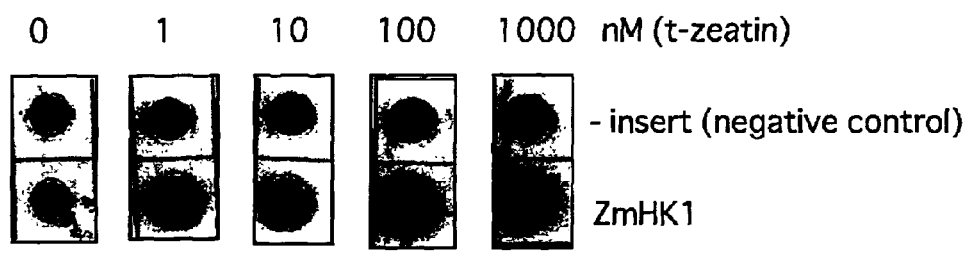
FIG. 2 presents photographs showing the experimental results of Example 5.

*E. coli* suspension was prepared in the same manner as in Example 4. Subsequently, the suspension was spotted on LAGX agar medium containing t-zeatin at varied concentrations from 0 nM to 1000 nM, and cultured overnight (12 hr) at 25° C. The next day, the color of each colony was observed. FIG. 2 shows the sate of each colony.

As shown in FIG. 2, it has become clear that ZmHK1-transferred *E. coli* responds to t-zeatin at a concentration of 10 μM or less. This indicates that ZmHK1-transferred *E. coli* is able to respond to a cytokinin of lower concentrations at least under these experimental conditions.

EXAMPLE 6

Examination of Biosensor Function (1)

A suspension of the *E. coli* transformant prepared in Example 1 and a suspension of the *E. coli* transformant prepared in Example 4 were mixed. Then, whether the mixture of these two transformants can function as a biosensor or not was examined.

Figure 3:
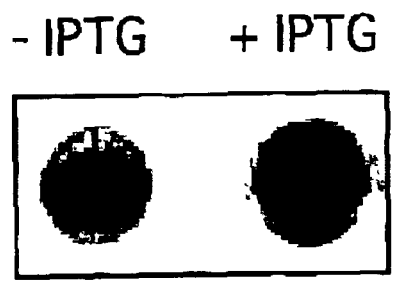
FIG. 3 presents photographs showing the experimental results of Example 6.
Figure 3:
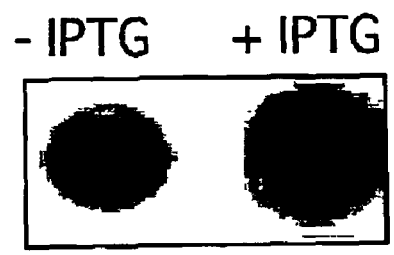

Briefly, *E. coli* [pTrcIPT7] or *E. coli* [pTrcIPT8] prepared in Example 1 and *E. coli* [pIN-III-ZmHK1] prepared in Example 4 were cultured separately in 2 ml of modified M9 minimum medium overnight at 25° C. Subsequently, 0.5 ml of the overnight culture of *E. coli* [pTrcIPT7] or *E. coli* [pTrcIPT8] was added to 10 ml of fresh modified M9 minimum medium and cultured until ABSORBANCE AT 600 NM reached 0.5, followed by addition of IPTG to give a concentration of 1 mM. Then, cells were cultured for another 4 hr at 25° C. As a control, cells were cultured without addition of IPTG. The overnight culture of *E. coli* [pIN-III-ZmHK1] was centrifuged and the supernatant was discarded. The *E coli* cell pellet was washed in sterilized water twice and suspended in 2 ml (final volume) of sterilized water. A suspension of *E. coli* [pTrcIPT7] or *E. coli* [pTrcIPT8] after cultivation was mixed with the suspension of *E. coli* [pIN-III-ZmHK1] (1:1 in volume), and 10 μl of the mixed suspension was spotted on LAGX agar medium, followed by overnight cultivation at room temperature (25° C.). The next day, the color of each colony was observed. FIG. 3 shows the state of each colony.

EXAMPLE 7

Examination of Biosensor Function (2)

A culture supernatant of the *E. coli* transformant prepared in Example 1 and a suspension of the *E. coli* transformant prepared in Example 4 were mixed. Then, whether the mixture of these two transformants can function as a biosensor or not was examined.

Figure 4:
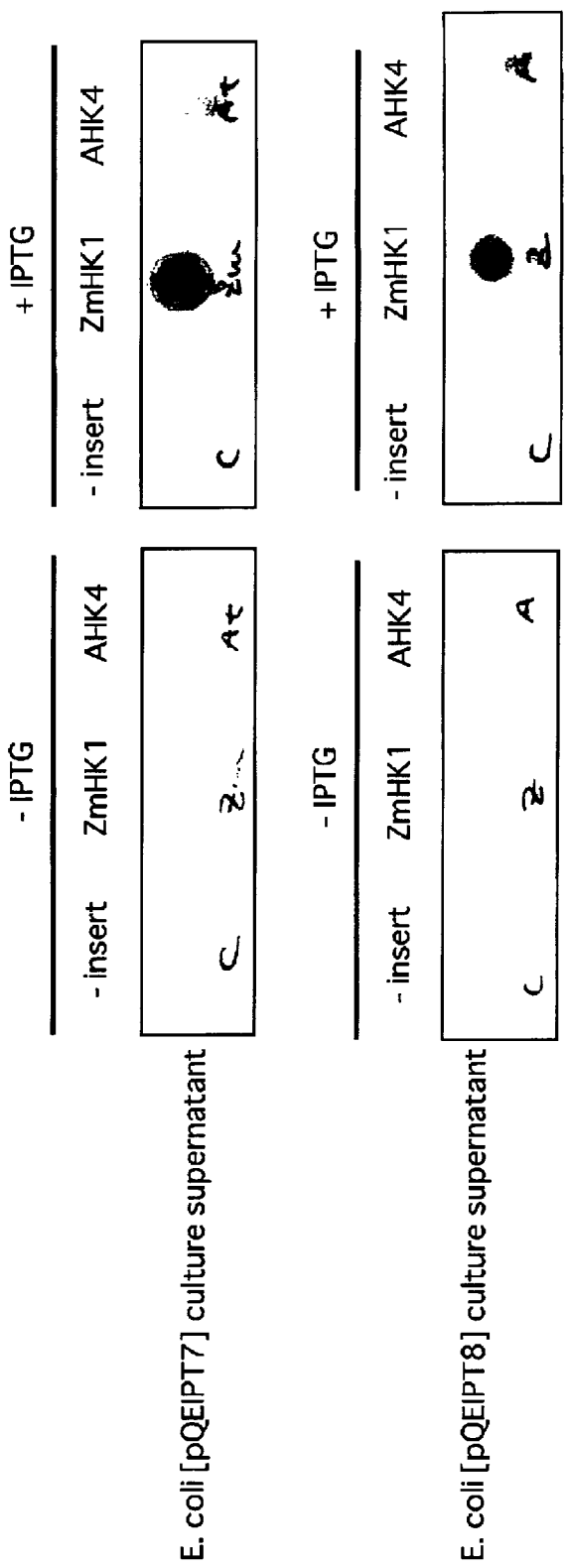
FIG. 4 presents photographs showing the experimental results of Example 7.

Briefly, *E. coli* [pTrcIPT7] or *E. coli* [pTrcIPT8] prepared in Example 1 and *E. coli* [pIN-III-ZmHK1] prepared in Example 4 were cultured separately in 2 ml of modified M9 minimum medium overnight at 25° C. Subsequently, 0.5 ml of the overnight culture of *E. coli* [pTrcIPT7] or *E. coli* [pTrcIPT8] was added to 10 ml of fresh modified M9 minimum medium and cultured until ABSORBANCE AT 600 NM reached 0.5, followed by addition of IPTG to give a concentration of 1 mM. Then, cells were cultured for another 4 hr at 25° C. As a control, cells were cultured without addition of IPTG. The overnight culture of *E. coli* [pIN-III-ZmHKI] was centrifuged and the supernatant was discarded. The *E. coli* cell pellet was washed in sterilized water twice and suspended in 2 ml (final volume) of sterilized water. On the other hand, the culture broth of *E. coli* [pTrcIPT7] or *E. coli* [pTrcIPT8] was centrifuged at 3000×g for 10 min, and the supernatant was recovered. One milliliter of this supernatant was filtrated into LAGX agar medium uniformly. Since the volume of this agar medium is 20 mL, the cytokinin concentrations are estimated to become about ½₀ of the initial concentrations. On the resultant agar medium, 10 μl of the suspension of *E. coli* [pIN-III-ZmHK1] was spotted and cultured overnight at room temperature (25° C.). The next day, the color of each colony was observed. FIG. 4 shows the state of each colony.

The cytokinin contents in the culture supernatant of *E. coli* [pQEIPT7] or *E. coli* [pQEIPT7] after IPTG induction are as shown in Table 7. Since this culture supernatant was infiltrated into the above-described LAGX agar medium, the cytokinin concentrations in the agar medium are calculated as follows: approx. 41 nM iP and 3.4 nM t-zeatin when the culture supernatant of *E. coli* [pQEIPT7] was used; and approx. 25 nM iP and 0.4 nM t-zeatin when the culture supernatant of *E. coli* [pQEIPT7] was used.

In both Example 6 and Example 7, the ZmHK1-transferred transformant discriminated the presence or absence of a specific substance (IPTG in these Examples). A series of reactions, i.e. perception of an external environmental factor→synthesis of cytokinins→perception of the cytokinins→expression of a color development gene, occurred. Finally, the *E. coli* colony was observed to become blue. Since a commercially available substance recognition/control system was used in these experiments, a high concentration (1 mM) sample was necessary. By replacing this system with an appropriate one, it is possible to obtain substrate specificity and detection sensitivity that match the purpose of intended measurement. In these experiments, colonies did not present a blue color when the gene encoding AHK4 (a cytokinin receptor of *Arabidopsis thaliana*) was transferred. It is believed that AHK4 is unable to respond to cytokinins at concentrations of 50 nM or below under the above-described conditions probably because AHK4 is less sensitive than ZMHK1.

The entire disclosure of Japanese Patent Application No. 2001-291059 filed on Sep. 25, 2001 including specification, claims, drawings and summary is incorporated herein by reference in its entity.

All publications, patents and patent applications cited herein are incorporated herein by reference in their entity.

Effect of the Invention

The present invention provides a novel microorganism mixture and a novel microorganism for use in the measurement of environmental factors. By using this microorganism mixture or microorganism, it becomes possible to measure environmental factors simply and with high accuracy.

SEQUENCE LISTING

<160> NUMBER OF SEQ ID NOS: 50

<210> SEQ ID NO 1
<211> LENGTH: 3041
<212> TYPE: DNA
<213> ORGANISM: Zea mays
<220> FEATURE:
<221> NAME/KEY: CDS
<222> LOCATION: (77)..(2998)

<400> SEQUENCE: 1

```
gggcactggg cggggaata aggaggaaga gaaagaggag gaggagcggc agtagatttg        60
ggccgcacag gcaggg atg ggg ggc aag tac cgc gcg gcg agg acg aag agg       112
                 Met Gly Gly Lys Tyr Arg Ala Ala Arg Thr Lys Arg
                  1               5                  10 tgg tgg agg ggg ctg gca gcg gcc ggg tgg gtg cta acc gcg gtg gtc          160
Trp Trp Arg Gly Leu Ala Ala Ala Gly Trp Val Leu Thr Ala Val Val
         15                  20                  25 tgc tcc gcg gtg atg cac tgg acc ctg cgc cgg gac agc atg gac cgc          208
Cys Ser Ala Val Met His Trp Thr Leu Arg Arg Asp Ser Met Asp Arg
     30                  35                  40 gcc gag gag cgc ctc gtc agc atg tgc gag gag agg gcc agg atg ctg          256
Ala Glu Glu Arg Leu Val Ser Met Cys Glu Glu Arg Ala Arg Met Leu
 45                  50                  55                  60 cag gag cag ttc ggg gtc acc gtc aac cac gtc cac gcc atc gcc att          304
Gln Glu Gln Phe Gly Val Thr Val Asn His Val His Ala Ile Ala Ile
```

-continued

```
                 65                   70                   75
ctc atc tcc acc ttc aac ttc gag aag tcc cct cca gcc atc gac cag    352
Leu Ile Ser Thr Phe Asn Phe Glu Lys Ser Pro Pro Ala Ile Asp Gln
             80                   85                   90 gac acc ttt gca aaa tac acg gca agg aca tca ttt gag cga ccg ctg    400
Asp Thr Phe Ala Lys Tyr Thr Ala Arg Thr Ser Phe Glu Arg Pro Leu
         95                  100                  105 ctc aat ggg gtg gca ttc gca cag cgt gta ttc cat cat gag agg gaa    448
Leu Asn Gly Val Ala Phe Ala Gln Arg Val Phe His His Glu Arg Glu
    110                  115                  120 atg ttt gaa agc cag cag gga tgg gtt atg aat acg atg cag cgg gag    496
Met Phe Glu Ser Gln Gln Gly Trp Val Met Asn Thr Met Gln Arg Glu
125                  130                  135                  140 cct gca cct ccg cag gtt gaa tac gcc cca gtg att ttc tct cag gat    544
Pro Ala Pro Pro Gln Val Glu Tyr Ala Pro Val Ile Phe Ser Gln Asp
                 145                  150                  155 acg gtt tcc tac ctt gca cgc att gac atg atg tct ggg gag gag gac    592
Thr Val Ser Tyr Leu Ala Arg Ile Asp Met Met Ser Gly Glu Glu Asp
             160                  165                  170 cga gaa aac att ttc cgg gcc agg act act ggc aaa gct gtg tta aca    640
Arg Glu Asn Ile Phe Arg Ala Arg Thr Thr Gly Lys Ala Val Leu Thr
         175                  180                  185 aac cca ttt cgg ttg ctt gga tca aac cac ttg gga gta gtt ctc acg    688
Asn Pro Phe Arg Leu Leu Gly Ser Asn His Leu Gly Val Val Leu Thr
    190                  195                  200 ttt gct gtg tac cgc cct gat ctc cct gct gat gca tca gtt gag caa    736
Phe Ala Val Tyr Arg Pro Asp Leu Pro Ala Asp Ala Ser Val Glu Gln
205                  210                  215                  220 cgt gtg gaa gca act atc gga tat ctc ggt gga gcc ttt gat gtg gag    784
Arg Val Glu Ala Thr Ile Gly Tyr Leu Gly Gly Ala Phe Asp Val Glu
                 225                  230                  235 tca ctt gtg gag aat ttg ttg agc aaa ctt gct ggc aat cag gat att    832
Ser Leu Val Glu Asn Leu Leu Ser Lys Leu Ala Gly Asn Gln Asp Ile
             240                  245                  250 gtg gta aat gtc tat gat gtc aca aat gct tca gat gct atg gtt ttg    880
Val Val Asn Val Tyr Asp Val Thr Asn Ala Ser Asp Ala Met Val Leu
         255                  260                  265 tat gga cct tca agt ttg gac gag caa gtg cct ttc ttg cat gtt agc    928
Tyr Gly Pro Ser Ser Leu Asp Glu Gln Val Pro Phe Leu His Val Ser
    270                  275                  280 atg ttg gat ttt gga gat cca ttt agg aag cat gaa atg aga tgc agg    976
Met Leu Asp Phe Gly Asp Pro Phe Arg Lys His Glu Met Arg Cys Arg
285                  290                  295                  300 tat aga caa aag ctt cct atg ccg tgg tct gcc ata acc aat cct ttg    1024
Tyr Arg Gln Lys Leu Pro Met Pro Trp Ser Ala Ile Thr Asn Pro Leu
                 305                  310                  315 ggc aca ttt gtc ata tgg atg ctt ctt ggg tat agc att gct gct gca    1072
Gly Thr Phe Val Ile Trp Met Leu Leu Gly Tyr Ser Ile Ala Ala Ala
             320                  325                  330 tat tct cga tat gac aaa gtt act gaa gat tgc aga aag atg gaa gag    1120
Tyr Ser Arg Tyr Asp Lys Val Thr Glu Asp Cys Arg Lys Met Glu Glu
         335                  340                  345 cta aaa acg cag gca gaa gct gct gat gtt gca aaa tct cag ttc ctg    1168
Leu Lys Thr Gln Ala Glu Ala Ala Asp Val Ala Lys Ser Gln Phe Leu
    350                  355                  360 gca act gcg tca cat gag atc aga aca cct atg aat ggc gtc ctt gga    1216
Ala Thr Ala Ser His Glu Ile Arg Thr Pro Met Asn Gly Val Leu Gly
365                  370                  375                  380 atg ctg gat atg ctt tta gga aca gat cta act atg aca cag aag gat    1264
Met Leu Asp Met Leu Leu Gly Thr Asp Leu Thr Met Thr Gln Lys Asp
```

```
                Met Leu Asp Met Leu Leu Gly Thr Asp Leu Thr Met Thr Gln Lys Asp
                            385                 390                 395 tat gct caa act gct caa atg tgt ggc aga gca ttg att aca ctg ata         1312
Tyr Ala Gln Thr Ala Gln Met Cys Gly Arg Ala Leu Ile Thr Leu Ile
            400                 405                 410 aat gat gtc ctt gat cga gca aag att gag gct gga aag tta gag ctt         1360
Asn Asp Val Leu Asp Arg Ala Lys Ile Glu Ala Gly Lys Leu Glu Leu
            415                 420                 425 gaa gcg gtg cct ttt gac ctg cgt tct ctc atg gat gat gtt gtt tcc         1408
Glu Ala Val Pro Phe Asp Leu Arg Ser Leu Met Asp Asp Val Val Ser
    430                 435                 440 ttg ttt tct tca aag tca cgg gag aag tgc att gag ctt gcc gta ttt         1456
Leu Phe Ser Ser Lys Ser Arg Glu Lys Cys Ile Glu Leu Ala Val Phe
445                 450                 455                 460 gta tgt gac aat gtt ccg aag gtt gtt att gga gat cct tgg agg ttt         1504
Val Cys Asp Asn Val Pro Lys Val Val Ile Gly Asp Pro Trp Arg Phe
                465                 470                 475 cga cag ata ctg aca aat ttg gtc ggg aat gca gtc aaa ttc aca gaa         1552
Arg Gln Ile Leu Thr Asn Leu Val Gly Asn Ala Val Lys Phe Thr Glu
            480                 485                 490 cga ggt cat gta ttt gtg cgg gtg tgt ttg gct gaa aac tca aat atg         1600
Arg Gly His Val Phe Val Arg Val Cys Leu Ala Glu Asn Ser Asn Met
            495                 500                 505 gaa gcc aat cag gtc cta cat gga gcc atg aat ggc aaa ggt ggt aga         1648
Glu Ala Asn Gln Val Leu His Gly Ala Met Asn Gly Lys Gly Gly Arg
    510                 515                 520 gtt gag tca aca gct aat ggt gcc ttc aat act ttg agt ggg ttt gaa         1696
Val Glu Ser Thr Ala Asn Gly Ala Phe Asn Thr Leu Ser Gly Phe Glu
525                 530                 535                 540 gca gca gac aga cga aat agt tgg caa tat ttt aaa ctg ctc ctc tct         1744
Ala Ala Asp Arg Arg Asn Ser Trp Gln Tyr Phe Lys Leu Leu Leu Ser
                545                 550                 555 gat aag gag tcg ctt ttg gat gat ctt gag agc gaa aac tct aat caa         1792
Asp Lys Glu Ser Leu Leu Asp Asp Leu Glu Ser Glu Asn Ser Asn Gln
            560                 565                 570 agt gat tca gat cgt gtc aca cta gca ata agt att gag gac aca ggt         1840
Ser Asp Ser Asp Arg Val Thr Leu Ala Ile Ser Ile Glu Asp Thr Gly
            575                 580                 585 gtc ggg ata cca ctg caa gca caa gat cgt gtt ttt aca ccg ttt atg         1888
Val Gly Ile Pro Leu Gln Ala Gln Asp Arg Val Phe Thr Pro Phe Met
    590                 595                 600 cag gct gac agt tca act tca agg aat tat ggc ggt act ggc atc ggt         1936
Gln Ala Asp Ser Ser Thr Ser Arg Asn Tyr Gly Gly Thr Gly Ile Gly
605                 610                 615                 620 tta agc atc agc aag tgt cta gct gaa ctt atg ggt ggg cag ata agt         1984
Leu Ser Ile Ser Lys Cys Leu Ala Glu Leu Met Gly Gly Gln Ile Ser
                625                 630                 635 ttc acc agc cat cct tct gtt gga agc acg ttc act ttc tca gcc aca         2032
Phe Thr Ser His Pro Ser Val Gly Ser Thr Phe Thr Phe Ser Ala Thr
            640                 645                 650 ctg aag cac tca cac aaa gat att tcg ggt gat tca agt agg agc ttg         2080
Leu Lys His Ser His Lys Asp Ile Ser Gly Asp Ser Ser Arg Ser Leu
            655                 660                 665 aca gag gca cta cca acc gct ttt aag gga atg aag gcc atc ttg gta         2128
Thr Glu Ala Leu Pro Thr Ala Phe Lys Gly Met Lys Ala Ile Leu Val
    670                 675                 680 gat ggg aga cct gta cgt agt gct gtt aca aga tat cac ctc aag agg         2176
Asp Gly Arg Pro Val Arg Ser Ala Val Thr Arg Tyr His Leu Lys Arg
685                 690                 695                 700
```

```
ttg gga ata ctt ctt caa gtt gtg aac aat atg aac gca gta gta aaa    2224
Leu Gly Ile Leu Leu Gln Val Val Asn Asn Met Asn Ala Val Val Lys
            705                 710                 715 gct ttc cca gga caa aat gga gca gcc ggt tct agg gaa aag gca tca    2272
Ala Phe Pro Gly Gln Asn Gly Ala Ala Gly Ser Arg Glu Lys Ala Ser
        720                 725                 730 att ctt ttt att gag agt gac ttc tgg agg cct gag aca gat gtt cag    2320
Ile Leu Phe Ile Glu Ser Asp Phe Trp Arg Pro Glu Thr Asp Val Gln
    735                 740                 745 tta ttg aac cat cta cgt gag cag aag aac ggt cag ttg tct gat ggg    2368
Leu Leu Asn His Leu Arg Glu Gln Lys Asn Gly Gln Leu Ser Asp Gly
750                 755                 760 cac aag gta gtt ctt ttg gtc acc tct gaa gcc gac aag gac aaa tat    2416
His Lys Val Val Leu Leu Val Thr Ser Glu Ala Asp Lys Asp Lys Tyr
765                 770                 775                 780 gga tcc ata ttt gat att gtg atg tgt aag cct ata agg gca agc aca    2464
Gly Ser Ile Phe Asp Ile Val Met Cys Lys Pro Ile Arg Ala Ser Thr
            785                 790                 795 att gct tca tct att caa caa ctg ctc aaa gta gag ata gcc gaa aga    2512
Ile Ala Ser Ser Ile Gln Gln Leu Leu Lys Val Glu Ile Ala Glu Arg
        800                 805                 810 aaa gat aat caa aac cgg ccg tcg ttc ctt cga agc ttg ctg gtt ggg    2560
Lys Asp Asn Gln Asn Arg Pro Ser Phe Leu Arg Ser Leu Leu Val Gly
    815                 820                 825 aag aat ata ttg gtc gta gac gat aat aaa gtc aac ctc aga gtt gct    2608
Lys Asn Ile Leu Val Val Asp Asp Asn Lys Val Asn Leu Arg Val Ala
830                 835                 840 gcg gct gca ctc aag aag tat ggt gct aat gtt agc tgt gtt gaa agc    2656
Ala Ala Ala Leu Lys Lys Tyr Gly Ala Asn Val Ser Cys Val Glu Ser
845                 850                 855                 860 ggc aag gat gct atc agt cta ctt caa ccc ccg cat cgc ttc gat gca    2704
Gly Lys Asp Ala Ile Ser Leu Leu Gln Pro Pro His Arg Phe Asp Ala
            865                 870                 875 tgt ttt atg gat gtt cag atg cca gag atg gac ggg ttt gag gca acc    2752
Cys Phe Met Asp Val Gln Met Pro Glu Met Asp Gly Phe Glu Ala Thr
        880                 885                 890 gga caa ata agg caa atg gag ttg aaa gcg aac gag gaa agg aag aac    2800
Gly Gln Ile Arg Gln Met Glu Leu Lys Ala Asn Glu Glu Arg Lys Asn
    895                 900                 905 aag ttg gct tcg atc gaa ggc tcg aca act gcc gag tac cat ctg cct    2848
Lys Leu Ala Ser Ile Glu Gly Ser Thr Thr Ala Glu Tyr His Leu Pro
910                 915                 920 gtt ctg gca atg aca gcc gat gtt atc cag gca act tac gaa gag tgc    2896
Val Leu Ala Met Thr Ala Asp Val Ile Gln Ala Thr Tyr Glu Glu Cys
925                 930                 935                 940 ata aaa tcg gga atg gat gga tac gta tct aaa ccc ttc gac gag gag    2944
Ile Lys Ser Gly Met Asp Gly Tyr Val Ser Lys Pro Phe Asp Glu Glu
            945                 950                 955 cag cta tac caa gca gtc tcc aga ttg gta gtg gga acg aca gat tcg    2992
Gln Leu Tyr Gln Ala Val Ser Arg Leu Val Val Gly Thr Thr Asp Ser
        960                 965                 970 gct gtt tgatgttcaa aatacgatgg accggacttc tcattcatca atc           3041
Ala Val
```

<210> SEQ ID NO 2
<211> LENGTH: 974
<212> TYPE: PRT
<213> ORGANISM: Zea mays

<400> SEQUENCE: 2

-continued

```
Met Gly Gly Lys Tyr Arg Ala Ala Arg Thr Lys Arg Trp Trp Arg Gly
 1               5                  10                  15

Leu Ala Ala Ala Gly Trp Val Leu Thr Ala Val Val Cys Ser Ala Val
             20                  25                  30

Met His Trp Thr Leu Arg Arg Asp Ser Met Asp Arg Ala Glu Glu Arg
         35                  40                  45

Leu Val Ser Met Cys Glu Glu Arg Ala Arg Met Leu Gln Glu Gln Phe
     50                  55                  60

Gly Val Thr Val Asn His Val His Ala Ile Ala Ile Leu Ile Ser Thr
 65                  70                  75                  80

Phe Asn Phe Glu Lys Ser Pro Pro Ala Ile Asp Gln Asp Thr Phe Ala
                 85                  90                  95

Lys Tyr Thr Ala Arg Thr Ser Phe Glu Arg Pro Leu Leu Asn Gly Val
             100                 105                 110

Ala Phe Ala Gln Arg Val Phe His His Glu Arg Glu Met Phe Glu Ser
         115                 120                 125

Gln Gln Gly Trp Val Met Asn Thr Met Gln Arg Glu Pro Ala Pro Pro
     130                 135                 140

Gln Val Glu Tyr Ala Pro Val Ile Phe Ser Gln Asp Thr Val Ser Tyr
145                 150                 155                 160

Leu Ala Arg Ile Asp Met Met Ser Gly Glu Glu Asp Arg Glu Asn Ile
                 165                 170                 175

Phe Arg Ala Arg Thr Thr Gly Lys Ala Val Leu Thr Asn Pro Phe Arg
             180                 185                 190

Leu Leu Gly Ser Asn His Leu Gly Val Val Leu Thr Phe Ala Val Tyr
         195                 200                 205

Arg Pro Asp Leu Pro Ala Asp Ala Ser Val Gln Arg Val Glu Ala
     210                 215                 220

Thr Ile Gly Tyr Leu Gly Gly Ala Phe Asp Val Glu Ser Leu Val Glu
225                 230                 235                 240

Asn Leu Leu Ser Lys Leu Ala Gly Asn Gln Asp Ile Val Val Asn Val
                 245                 250                 255

Tyr Asp Val Thr Asn Ala Ser Asp Ala Met Val Leu Tyr Gly Pro Ser
             260                 265                 270

Ser Leu Asp Glu Gln Val Pro Phe Leu His Val Ser Met Leu Asp Phe
     275                 280                 285

Gly Asp Pro Phe Arg Lys His Glu Met Arg Cys Arg Tyr Arg Gln Lys
290                 295                 300

Leu Pro Met Pro Trp Ser Ala Ile Thr Asn Pro Leu Gly Thr Phe Val
305                 310                 315                 320

Ile Trp Met Leu Leu Gly Tyr Ser Ile Ala Ala Tyr Ser Arg Tyr
                 325                 330                 335

Asp Lys Val Thr Glu Asp Cys Arg Lys Met Glu Glu Leu Lys Thr Gln
             340                 345                 350

Ala Glu Ala Ala Asp Val Ala Lys Ser Gln Phe Leu Ala Thr Ala Ser
         355                 360                 365

His Glu Ile Arg Thr Pro Met Asn Gly Val Leu Gly Met Leu Asp Met
     370                 375                 380

Leu Leu Gly Thr Asp Leu Thr Met Thr Gln Lys Asp Tyr Ala Gln Thr
385                 390                 395                 400

Ala Gln Met Cys Gly Arg Ala Leu Ile Thr Leu Ile Asn Asp Val Leu
                 405                 410                 415

Asp Arg Ala Lys Ile Glu Ala Gly Lys Leu Glu Leu Glu Ala Val Pro
```

-continued

```
                420                 425                 430
Phe Asp Leu Arg Ser Leu Met Asp Asp Val Val Ser Leu Phe Ser Ser
            435                 440                 445
Lys Ser Arg Glu Lys Cys Ile Glu Leu Ala Val Phe Val Cys Asp Asn
450                 455                 460
Val Pro Lys Val Val Ile Gly Asp Pro Trp Arg Phe Arg Gln Ile Leu
465                 470                 475                 480
Thr Asn Leu Val Gly Asn Ala Val Lys Phe Thr Glu Arg Gly His Val
                485                 490                 495
Phe Val Arg Val Cys Leu Ala Glu Asn Ser Asn Met Glu Ala Asn Gln
            500                 505                 510
Val Leu His Gly Ala Met Asn Gly Lys Gly Gly Arg Val Glu Ser Thr
            515                 520                 525
Ala Asn Gly Ala Phe Asn Thr Leu Ser Gly Phe Glu Ala Ala Asp Arg
            530                 535                 540
Arg Asn Ser Trp Gln Tyr Phe Lys Leu Leu Leu Ser Asp Lys Glu Ser
545                 550                 555                 560
Leu Leu Asp Asp Leu Glu Ser Glu Asn Ser Asn Gln Ser Asp Ser Asp
                565                 570                 575
Arg Val Thr Leu Ala Ile Ser Ile Glu Asp Thr Gly Val Gly Ile Pro
            580                 585                 590
Leu Gln Ala Gln Asp Arg Val Phe Thr Pro Phe Met Gln Ala Asp Ser
        595                 600                 605
Ser Thr Ser Arg Asn Tyr Gly Gly Thr Gly Ile Gly Leu Ser Ile Ser
    610                 615                 620
Lys Cys Leu Ala Glu Leu Met Gly Gly Gln Ile Ser Phe Thr Ser His
625                 630                 635                 640
Pro Ser Val Gly Ser Thr Phe Thr Phe Ser Ala Thr Leu Lys His Ser
                645                 650                 655
His Lys Asp Ile Ser Gly Asp Ser Ser Arg Ser Leu Thr Glu Ala Leu
            660                 665                 670
Pro Thr Ala Phe Lys Gly Met Lys Ala Ile Leu Val Asp Gly Arg Pro
            675                 680                 685
Val Arg Ser Ala Val Thr Arg Tyr His Leu Lys Arg Leu Gly Ile Leu
690                 695                 700
Leu Gln Val Val Asn Asn Met Asn Ala Val Val Lys Ala Phe Pro Gly
705                 710                 715                 720
Gln Asn Gly Ala Ala Gly Ser Arg Glu Lys Ala Ser Ile Leu Phe Ile
                725                 730                 735
Glu Ser Asp Phe Trp Arg Pro Glu Thr Asp Val Gln Leu Leu Asn His
            740                 745                 750
Leu Arg Glu Gln Lys Asn Gly Gln Leu Ser Asp Gly His Lys Val Val
            755                 760                 765
Leu Leu Val Thr Ser Glu Ala Asp Lys Asp Lys Tyr Gly Ser Ile Phe
            770                 775                 780
Asp Ile Val Met Cys Lys Pro Ile Arg Ala Ser Thr Ile Ala Ser Ser
785                 790                 795                 800
Ile Gln Gln Leu Leu Lys Val Glu Ile Ala Glu Arg Lys Asp Asn Gln
                805                 810                 815
Asn Arg Pro Ser Phe Leu Arg Ser Leu Leu Val Gly Lys Asn Ile Leu
            820                 825                 830
Val Val Asp Asp Asn Lys Val Asn Leu Arg Val Ala Ala Ala Ala Leu
835                 840                 845
```

```
Lys Lys Tyr Gly Ala Asn Val Ser Cys Val Glu Ser Gly Lys Asp Ala
    850                 855                 860

Ile Ser Leu Leu Gln Pro Pro His Arg Phe Asp Ala Cys Phe Met Asp
865                 870                 875                 880

Val Gln Met Pro Glu Met Asp Gly Phe Glu Ala Thr Gly Gln Ile Arg
                885                 890                 895

Gln Met Glu Leu Lys Ala Asn Glu Glu Arg Lys Asn Lys Leu Ala Ser
            900                 905                 910

Ile Glu Gly Ser Thr Thr Ala Glu Tyr His Leu Pro Val Leu Ala Met
        915                 920                 925

Thr Ala Asp Val Ile Gln Ala Thr Tyr Glu Glu Cys Ile Lys Ser Gly
    930                 935                 940

Met Asp Gly Tyr Val Ser Lys Pro Phe Asp Glu Gln Leu Tyr Gln
945                 950                 955                 960

Ala Val Ser Arg Leu Val Val Gly Thr Thr Asp Ser Ala Val
            965                 970
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 3
tcatgacaga actcaacttc cacc                                           24

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 4
ataaagcttc taattttgca ccaaatgccg c                                   31

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 5
cgcggatcca tcatgattat gaagatatct atggc                               35

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 6
gcgctcgagc tgatcacgcc actagacacc g                                   31

<210> SEQ ID NO 7
```

```
<211> LENGTH: 24
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 7
tcatgaagtg taatgacaaa atgg                                              24

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 8
atagtcgacg ttttgcggtg atattagtcc                                        30

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 9
gggatcatga agccatgcat gacggc                                            26

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 10
gcgctcgagt tacctcaccg ggaaatcgc                                         29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 11
caacaactca tgaccttgtt atcacc                                            26

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 12
ggccaagctt ggaaaaacag actaaacttc c                                      31

<210> SEQ ID NO 13
<211> LENGTH: 31
```

```
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 13
ggcggatcct catgaagttc tcaatctcat c                               31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 14
ggcctgcagc ttttcatatc atattgtggg c                               31

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 15
caaaatctta cgtccacatt cgtctc                                     26

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 16
ccggctgcag ctcacacttt gtctttcacc                                 30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 17
cgcaaaaaac ccatggatct gcgtc                                      25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 18
cgaacatcgg atccaaatga agacagg                                    27

<210> SEQ ID NO 19
<211> LENGTH: 31
<212> TYPE: DNA
```

<213> ORGANISM: Artificial Sequence
<220> FEATURE:
<223> OTHER INFORMATION: Description of Artificial Sequence: SYNTHETIC DNA

<400> SEQUENCE: 19
ataggatccc taatgacaga actcaacttc c            31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 20
ataaagcttc taattttgca ccaaatgccg c            31

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 21
gcgggatcca tgatcatgaa gatatctatg g            31

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 22
gcgctcgagc tgatcacgcc actagacacc g            31

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 23
ataggtacca tttacgacat gaagtgtaat gac          33

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 24
atagtcgacg ttttgcggtg atattagtcc              30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 25
gcgggatcca tgaagccatg catgacggc                             29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 26
gcgctcgagt tacctcaccg ggaaatcgc                             29

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 27
gcgagatcta tgcaacaact catgacc                               27

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 28
gcgctcgagg gaaaaacaga ctaaacttcc                            30

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 29
gcgggatcca tgaagttctc aatctcatca c                          31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 30
gcgctcgagc ttttcatatc atattgtggg c                          31

<210> SEQ ID NO 31
<211> LENGTH: 29
<212> TYPE: DNA
<213> ORGANISM: Artificial Sequence
<220> FEATURE:

<223> OTHER INFORMATION: Description of Artificial Sequence: SYNTHETIC
      DNA

<400> SEQUENCE: 31
gcgggatcca tgcaaaatct tacgtccac                                              29

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 32
ccggctgcag ctcacacttt gtctgcgctc gagctcacac tttgtctttc acc                   53

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 33
gcgggatcca tgacagaact caacttccac c                                           31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 34
gcgctcgagc taattttgca ccaaatgccg c                                           31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 35
gcgggatcca tgatcatgaa gatatctatg g                                           31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 36
gcgctcgagc tgatcacgcc actagacacc g                                           31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: SYNTHETIC

DNA

<400> SEQUENCE: 37
gcgagatcta tgaagtgtaa tgacaaaatg g         31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 38
gcgctcgagt gttttgcggt gatattagtc c         31

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 39
gcgggatcca tgaagccatg catgacggc           29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 40
gcgctcgagt tacctcaccg ggaaatcgc           29

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 41
gcgagatcta tgcaacaact catgacc             27

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 42
gcgctcgagg gaaaaacaga ctaaacttcc          30

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 43
gcgggatcca tgaagttctc aatctcatca c                                31

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 44
gcgctcgagc ttttcatatc atattgtggg c                                31

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 45
gcgggatcca tgcaaaatct tacgtccac                                   29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 46
gcgctcgagc tcacactttg tctttcacc                                   29

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 47
gaagaacggt cagttgtcgg atg                                         23

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 48
gattgatgaa tgagaagtcc gg                                          22

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: SYNTHETIC
      DNA -continued

```
<400> SEQUENCE: 49
ctgatcagat gggggggcaag tacc                                     24

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      DNA

<400> SEQUENCE: 50
cctcgagtca aacagccgaa tct                                       23
```

Sequence Listing Free Text

SEQ ID NO: 3 shows the nucleotide sequence of a primer used for amplifying AtIPT1.

SEQ ID NO: 4 shows the nucleotide sequence of a primer used for amplifying AtIPT1.

SEQ ID NO: 5 shows the nucleotide sequence of a primer used for amplifying AtIPT3.

SEQ ID NO: 6 shows the nucleotide sequence of a primer used for amplifying AtIPT3.

SEQ ID NO: 7 shows the nucleotide sequence of a primer used for amplifying AtIPT4.

SEQ ID NO: 8 shows the nucleotide sequence of a primer used for amplifying AtIPT4.

SEQ ID NO: 9 shows the nucleotide sequence of a primer used for amplifying AtIPT5.

SEQ ID NO: 10 shows the nucleotide sequence of a primer used for amplifying AtIPT5.

SEQ ID NO: 11 shows the nucleotide sequence of a primer used for amplifying AtIPT6.

SEQ ID NO: 12 shows the nucleotide sequence of a primer used for amplifying AtIPT6.

SEQ ID NO: 13 shows the nucleotide sequence of a primer used for amplifying AtIPT7.

SEQ ID NO: 14 shows the nucleotide sequence of a primer used for amplifying AtIPT7.

SEQ ID NO: 15 shows the nucleotide sequence of a primer used for amplifying AtIPT8.

SEQ ID NO: 16 shows the nucleotide sequence of a primer used for amplifying AtIPT8.

SEQ ID NO: 17 shows the nucleotide sequence of a primer used for tmr.

SEQ ID NO: 18 shows the nucleotide sequence of a primer used for tmr.

SEQ ID NO: 19 shows the nucleotide sequence of a primer used for amplifying AtIPT1.

SEQ ID NO: 20 shows the nucleotide sequence of a primer used for amplifying AtIPT1.

SEQ ID NO: 21 shows the nucleotide sequence of a primer used for amplifying AtIPT3.

SEQ ID NO: 22 shows the nucleotide sequence of a primer used for amplifying AtIPT3.

SEQ ID NO: 23 shows the nucleotide sequence of a primer used for amplifying AtIPT4.

SEQ ID NO: 24 shows the nucleotide sequence of a primer used for amplifying AtIPT4.

SEQ ID NO: 25 shows the nucleotide sequence of a primer used for amplifying AtIPT5.

SEQ ID NO: 26 shows the nucleotide sequence of a primer used for amplifying AtIPT5.

SEQ ID NO: 27 shows the nucleotide sequence of a primer used for amplifying AtIPT6.

SEQ ID NO: 28 shows the nucleotide sequence of a primer used for amplifying AtIPT6.

SEQ ID NO: 29 shows the nucleotide sequence of a primer used for amplifying AtIPT7.

SEQ ID NO: 30 shows the nucleotide sequence of a primer used for amplifying AtIPT7.

SEQ ID NO: 31 shows the nucleotide sequence of a primer used for amplifying AtIPT8.

SEQ ID NO: 32 shows the nucleotide sequence of a primer used for amplifying AtIPT8.

SEQ ID NO: 33 shows the nucleotide sequence of a primer used for amplifying AtIPT1.

SEQ ID NO: 34 shows the nucleotide sequence of a primer used for amplifying AtIPT1.

SEQ ID NO: 35 shows the nucleotide sequence of a primer used for amplifying AtIPT3.

SEQ ID NO: 36 shows the nucleotide sequence of a primer used for amplifying AtIPT3.

SEQ ID NO: 37 shows the nucleotide sequence of a primer used for amplifying AtIPT4.

SEQ ID NO: 38 shows the nucleotide sequence of a primer used for amplifying AtIPT4.

SEQ ID NO: 39 shows the nucleotide sequence of a primer used for amplifying AtIPT5.

SEQ ID NO: 40 shows the nucleotide sequence of a primer used for amplifying AtIPT5.

SEQ ID NO: 41 shows the nucleotide sequence of a primer used for amplifying AtIPT6.

SEQ ID NO: 42 shows the nucleotide sequence of a primer used for amplifying AtIPT6.

SEQ ID NO: 43 shows the nucleotide sequence of a primer used for amplifying AtIPT7.

SEQ ID NO: 44 shows the nucleotide sequence of a primer used for amplifying AtIPT7.

SEQ ID NO: 45 shows the nucleotide sequence of a primer used for amplifying AtIPT8.

SEQ ID NO: 46 shows the nucleotide sequence of a primer used for amplifying AtIPT8.

SEQ ID NO: 47 shows the nucleotide sequence of a primer used in the amplification of a probe for isolating pZmHk1 clone.

SEQ ID NO: 48 shows the nucleotide sequence of a primer used in the amplification of a probe for isolating pZmHk1 clone.

SEQ ID NO: 49 shows the nucleotide sequence of a primer used in the amplifying the protein coding region of pZmHk1.

SEQ ID NO: 50 shows the nucleotide sequence of a primer used in the amplifying the protein coding region of pZmHk1.

What is claimed is:

1. A microorganism mixture consisting of a first microorganism that secretes a substance upon perception of an environmental factor and a second microorganism that expresses a marker gene upon perception of said substance secreted.

2. The microorganism mixture according to claim 1, wherein said first microorganism that secretes a substance upon perception of an environmental factor is a microorganism having a gene of an enzyme that synthesizes said substance and a mechanism that allows said gene to be expressed in response to said environmental factor.

3. The microorganism mixture according to claim 1, wherein said second microorganism that expresses a marker gene upon perception of said substance secreted is a microorganism having a mechanism that allows said marker gene to be expressed in response to said substance secreted.

4. The microorganism mixture according to claim 1, wherein said substance secreted is a plant hormone.

5. The microorganism mixture according to claim 5, wherein said plant hormone is a cytokinin.

6. The microorganism mixture according to claim 1, wherein said environmental factor is osmotic pressure, oxygen, phosphate ions, nickel ions or copper ions.

7. The microorganism that secretes a substance upon perception of an environmental factor and expresses a marker gene upon perception of said substance secreted.

8. The microorganism mixture according to claim 7, which is a microorganism having a gene of an enzyme that synthesizes said substance and a mechanism that allows said gene to be expressed in response to said environmental factor.

9. The microorganism mixture according to claim 7, which is a microorganism having a mechanism that allows said marker gene to be expressed in response to said substance secreted.

10. The microorganism mixture according to claim 7, wherein said substance secreted is a plant hormone.

11. The microorganism mixture according to claim 10, wherein said plant hormone is a cytokinin.

12. The microorganism according to claim 7, wherein said environmental factor is osmotic pressure, oxygen, phosphate ions, nitrate ions, nickel ions or copper ions.

13. A method of measuring an environmental factor, comprising mixing the microorganism mixture or the microorganism according to any one of claims 1 to 12 with a sample and measuring the environmental factor from the expression level of the marker gene.

14. The microorganism mixture according to claim 1, wherein the marker gene of the second microorganism comprises a pigment gene, a luminescent gene, or a fluoroscence gene.

15. The microorganism mixture according to claim 1, wherein the marker gene of the second microorganism comprises a β-galactosidase gene, a luciferase gene, or a green fluorescence protein (GFP) gene.

16. The microorganism according to claim 7, wherein the marker gene of the microorganism comprises a pigment gene, a luminescent gene, or a fluoroscene gene.

17. The microorganism according to claim 7, wherein the marker gene of the microorganism comprises a β-galactosidase gene, a luciferase gene, or a green fluorescence protein (GFP) gene.

18. The microorganism mixture according to claim 1, wherein the secreted substance comprises cytokinins, ethylene, auxins, or abscisic acid.

19. The microorganism according to claim 7, wherein the secreted substance comprises cytokinins, ethylene, auxins, or abscisic acid.

* * * * *

UNITED STATES PATENT AND TRADEMARK OFFICE
CERTIFICATE OF CORRECTION

PATENT NO.   : 6,893,825 B2
DATED        : May 17, 2005
INVENTOR(S)  : Hitoshi Sakakibara et al.

It is certified that error appears in the above-identified patent and that said Letters Patent is hereby corrected as shown below:

Column 45,
Line 20, delete "claim 5" to -- claim 4 --.
Line 25, delete "The microorganism" to -- A microorganism --.
Lines 27 and 33, delete "mixture".

Column 46,
Lines 1 and 3, delete "mixture".

Signed and Sealed this

Thirtieth Day of August, 2005

JON W. DUDAS
*Director of the United States Patent and Trademark Office*